(12) United States Patent
Tarassenko et al.

(10) Patent No.: US 7,318,808 B2
(45) Date of Patent: Jan. 15, 2008

(54) COMBINING MEASUREMENTS FROM BREATHING RATE SENSORS

(75) Inventors: Lionel Tarassenko, Oxford (GB); Catherine Laura Mason, Oxford (GB)

(73) Assignee: Isis Innovation Limited, Oxford (GB)

( * ) Notice: Subject to any disclaimer, the term of this patent is extended or adjusted under 35 U.S.C. 154(b) by 389 days.

(21) Appl. No.: 10/498,673

(22) PCT Filed: Dec. 13, 2002

(86) PCT No.: PCT/GB20/05684

§ 371 (c)(1), (2), (4) Date: Jul. 19, 2004

(87) PCT Pub. No.: WO03/051198

PCT Pub. Date: Jun. 26, 2003

(65) Prior Publication Data

US 2005/0027205 A1 Feb. 3, 2005

(30) Foreign Application Priority Data

Dec. 14, 2001 (GB) ................................. 0130010.2

(51) Int. Cl.
*A61B 5/02* (2006.01)
(52) U.S. Cl. .................. 600/529; 600/533; 600/538
(58) Field of Classification Search ................ 600/300, 600/481, 529
See application file for complete search history.

(56) References Cited

U.S. PATENT DOCUMENTS

| | | | |
|---|---|---|---|
| 4,791,573 A | 12/1988 | Zemany et al. | |
| 4,949,710 A | 8/1990 | Dorsett et al. | |
| 5,355,893 A | 10/1994 | Mick et al. | |
| 5,396,893 A | 3/1995 | Oberg et al. | |
| 5,626,140 A * | 5/1997 | Feldman et al. | 600/484 |
| 5,853,364 A | 12/1998 | Baker, Jr. et al. | |

(Continued)

FOREIGN PATENT DOCUMENTS

EP 0 434 856 A1 12/1989

(Continued)

OTHER PUBLICATIONS

Moody et al; "Clinical Validation of the ECG-Derived Respiration (EDR) Technique"; Computers in Cardiology 1986, vol. 13, pp. 507-510, Washington, DC, IEEE Computer Society Press, http://physionet.incor.usp.br/physiotools/edr/cic86.html.

(Continued)

*Primary Examiner*—Robert L. Kasser
(74) *Attorney, Agent, or Firm*—Nixon & Vanderhye PC

(57) ABSTRACT

A method for combining breathing rate measurements from two or more independent measurement channels. Independent measurements of breathing rate, for instance by impedance pneumography and photoplethysmography, can be combined to derive an improved measurement eliminating artefacts on one channel. A model of the process generating the breathing rate, is constructed and is run independently for each channel to generate predictions of the breathing rate. The model may be a Kalman filter. The measured values are compared with the predicted values and the difference is used as an indication of the confidence in the measurement, the higher the difference the lower the confidence. The measurements from the two channels are combined using weights calculated from the respected differences.

20 Claims, 8 Drawing Sheets

U.S. PATENT DOCUMENTS

| | | | |
|---|---|---|---|
| 5,919,141 | A | 7/1999 | Money et al. |
| 6,299,582 | B1 | 10/2001 | Brockway et al. |
| 6,839,659 | B2 | 1/2005 | Tarassenko et al. |
| 6,928,370 | B2 | 8/2005 | Anuzis et al. |
| 2003/0187337 | A1* | 10/2003 | Tarassenko et al. ......... 600/300 |
| 2004/0148140 | A1 | 7/2004 | Tarassenko et al. |
| 2005/0027205 | A1 | 3/2005 | Tarassenko et al. |

FOREIGN PATENT DOCUMENTS

| | | |
|---|---|---|
| EP | 0469794 A2 | 2/1992 |
| WO | 94 23495 | 10/1994 |
| WO | 00 27281 | 5/2000 |
| WO | 01/03231 A2 | 5/2001 |
| WO | 01/76471 A1 | 10/2001 |

OTHER PUBLICATIONS

Moody et al; Derivation of Respiratory Signals Form Multi-Lead ECGs; Computers in Cardiology, 1985, vol. 12, pp. 113-116, Washington, DC, IEEE Computer Society Press, http://physionet.incor.usp.br/physiotools/edr/cic86/edr86.html.

* cited by examiner

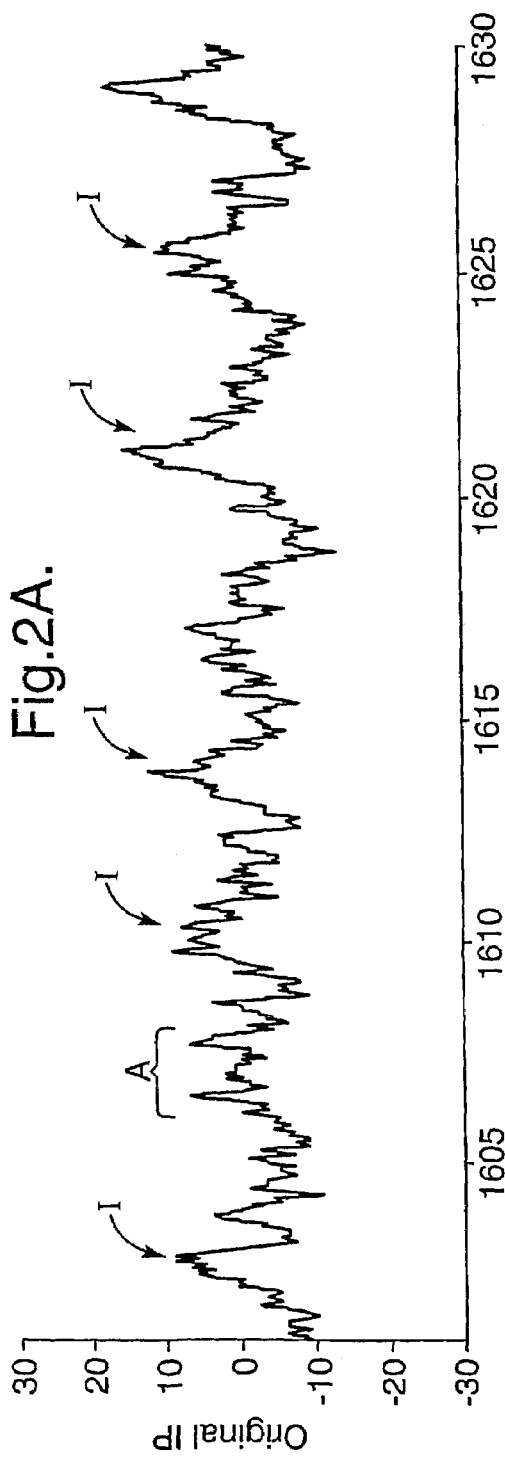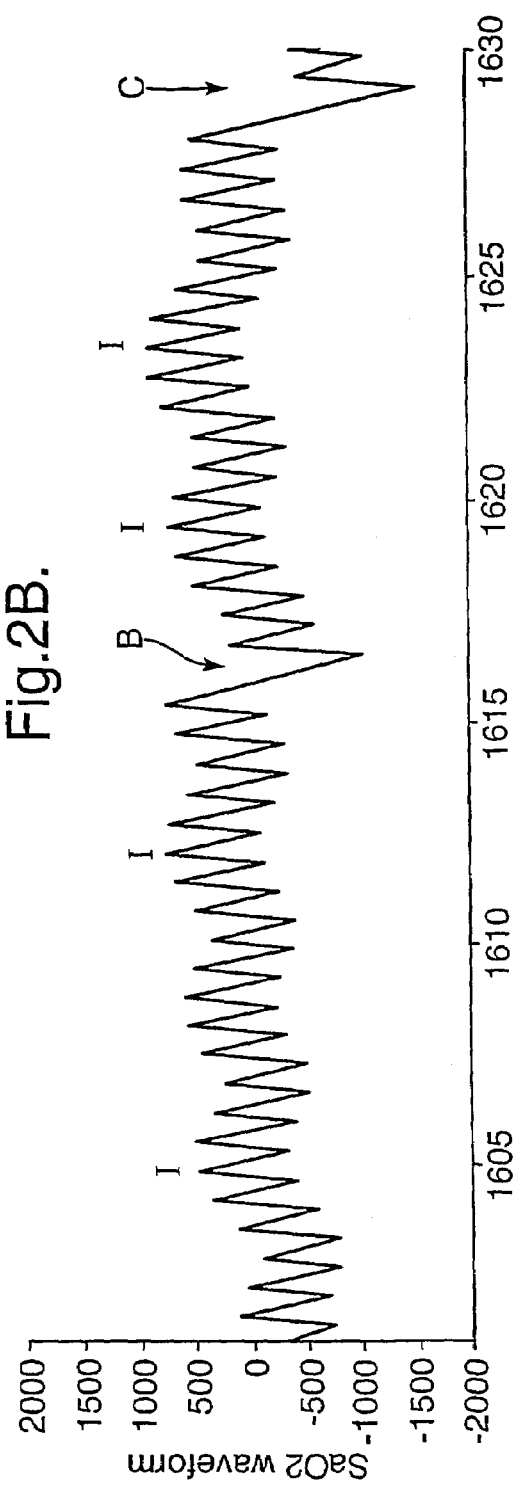
Fig.2A.
Fig.2B.

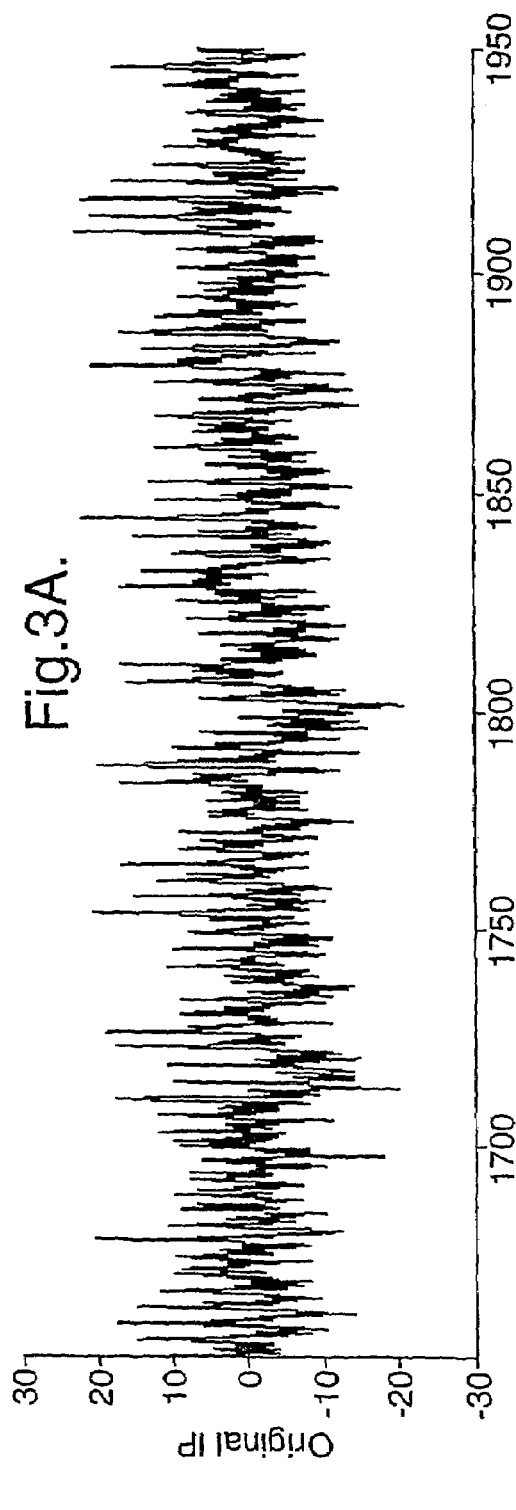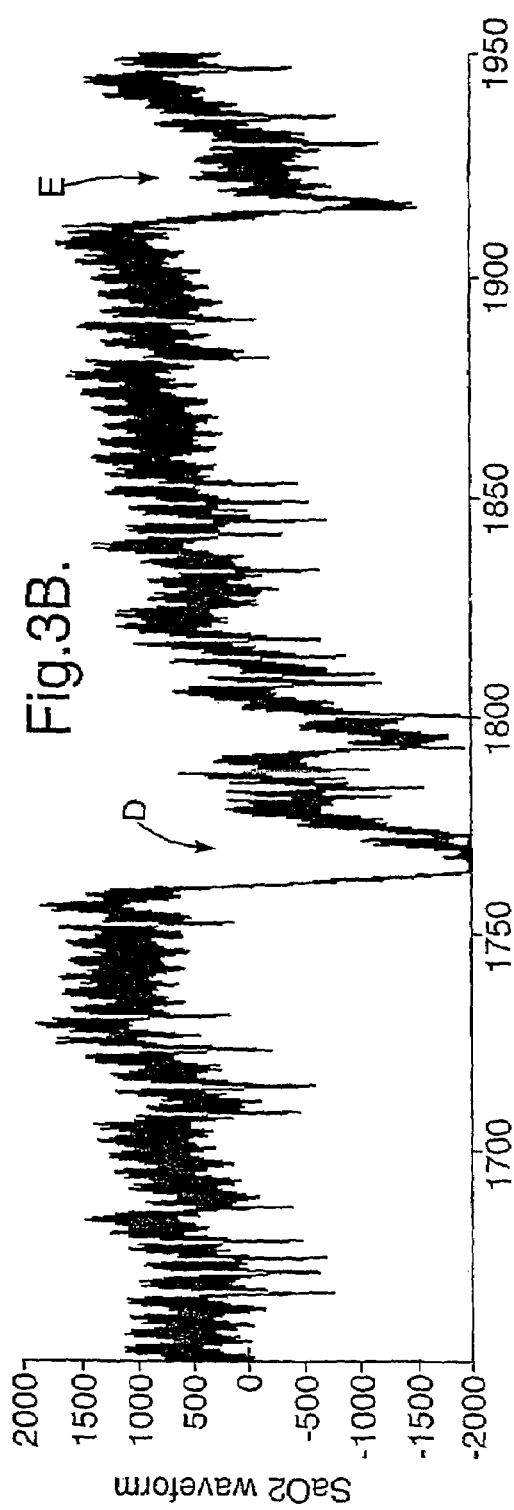
Fig. 3A.
Fig. 3B.

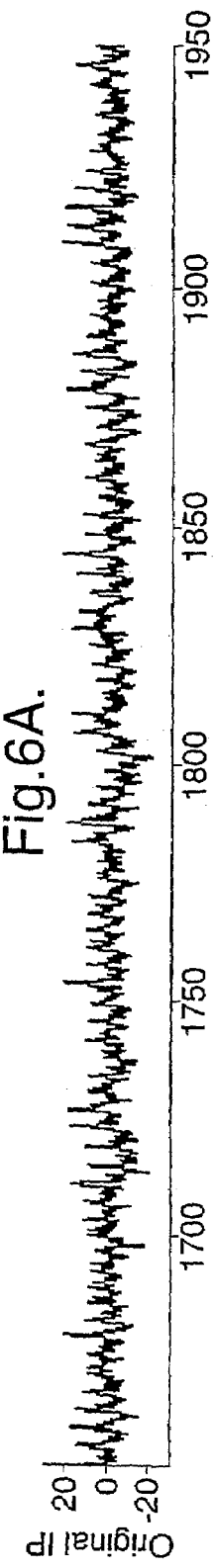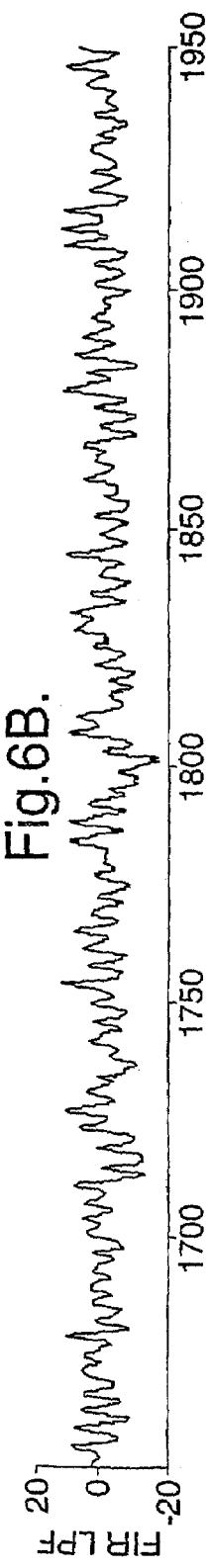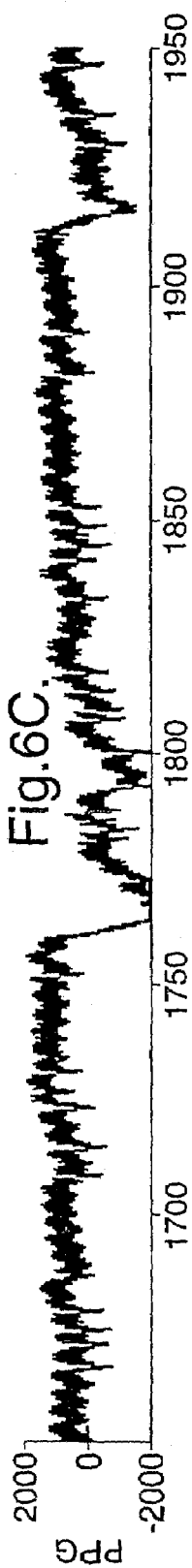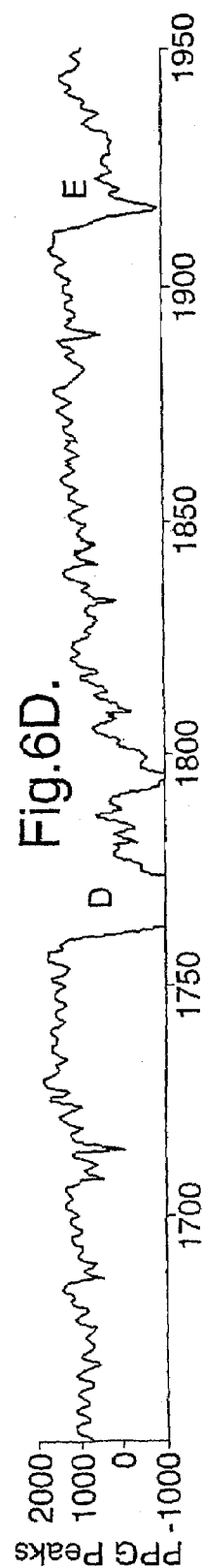

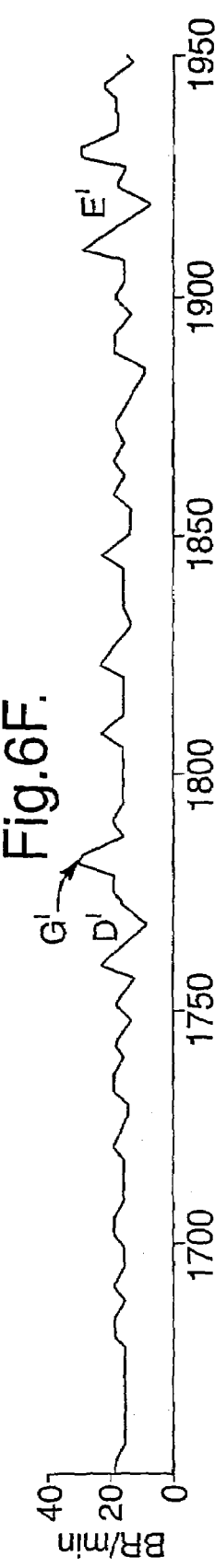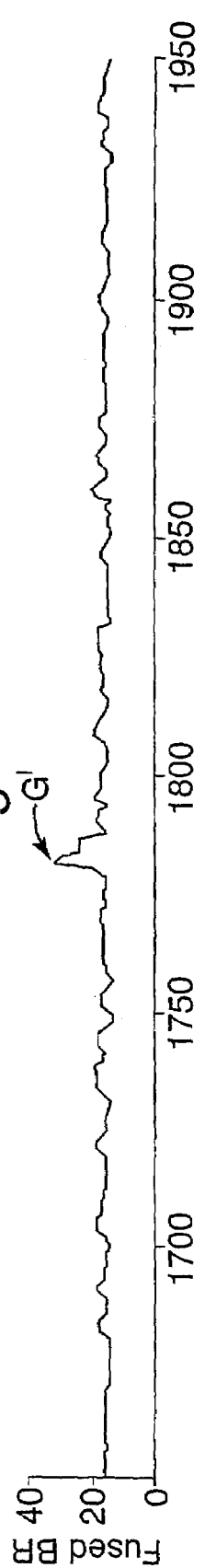

COMBINING MEASUREMENTS FROM BREATHING RATE SENSORS

This application is the US national phase of international application PCT/GB02/05684 filed 13 Dec. 2002, which designated the US. PCT/GB02/05684 claims priority to GB Application No. 0130010.2 filed 14 Dec. 2001. The entire contents of these applications are incorporated herein by reference.

BACKGROUND AND SUMMARY

The present invention relates to a method and apparatus for measuring the breathing rate of a subject, such as a human or animal, and in particular to a way of combining measurements from two or more breathing rate sensors in order to provide an improved measurement of breathing rate.

There is no clinically acceptable method for the non-invasive measurement of breathing rate. A nasal thermistor provides a simple and inexpensive means of tracking respiration but it is obtrusive and is not deemed to be acceptable for patients on the general ward or even the Coronary Care Unit (CCU). Electrical impedance plethysmography (also known as impedance pneumography) can be used to provide an indirect measure of respiration by measuring the changes in electrical impedance across the chest with breathing. In this method a small-amplitude, high-frequency current is injected into the body through a pair of surface electrodes and the resulting voltage is demodulated to obtain impedance measurements. The electrical impedance increases as high-resistivity air enters the lungs during inspiration but part of the change is also due to the movement of the electrodes on the chest wall. When monitored in a clinical environment, the impedance plethysmography (IP) signal is often very noisy and is seriously disrupted by patient movement or change in posture. As a consequence, it has not been considered reliable enough to provide respiration information for regular use on the ward.

Respiratory information is found in other signals recorded from patients with non-invasive sensors. For example, both the electrocardiogram (EGG) and photoplethysmogram (PPG) waveforms are modulated by the patient's breathing. The PPG signal represents the variation in light absorption across a finger or earlobe with every heart beat. This signal is measured at two wavelengths (usually in the red and near infra-red parts of the spectrum) in a standard pulse oximeter.

FIG. 2 shows 30-second sections of IP (FIG. 2A) and PPG (FIG. 2B) signals recorded from a patient in CCU. Referring first to the IP signal in FIG. 2A, the main peaks I, each corresponding to a breath, can be identified. However, changes in electrical impedance with the heart beat (as opposed to respiration) are apparent between t=1607 and t=1608 (marked as "A") and probably conceal a peak caused by a breath. Referring to FIG. 2B, the modulation of the PPG caused by respiration (marked "I") can be seen, although there are small movement artefacts B, C at t=1617 and t=1629. FIG. 3 shows the IP and PPG signals from the same patient, for a five-minute period. The effect, marked D, E, of movement artefact on the finger probe from which the PPG signal is recorded becomes very obvious at t=1770 and t=1920.

Clearly the artefacts caused by movement and heartbeat would affect the measurement of breathing rate from these signals. One might consider removing these artefacts by some type of filtering and thresholding.

FIG. 4B shows the effect of applying a Finite Impulse Response (FIR) low-pass filter with a pass-band cut-off at 0.33 Hz (corresponding to 20 breaths per minute) and a stop-band cut-off of 1 Hz (−50 dB) to the IP waveform of FIG. 4A. The cardiac-synchronous changes are filtered out (see the output of the filter between t=1605 and t=1610) and the respiratory cycle is clear. There are as many peaks (i.e. breaths) in FIG. 4B as there are in FIG. 4D, which shows the result of tracking the peaks of the PPG signal shown in FIG. 4C and interpolating (with straight lines) between each peak. The modulation envelope picked out by the peak tracking produces another respiratory waveform. The same information is again displayed on a five-minute timescale in FIG. 5. The breathing rate can be estimated by calculating the interval between two successive peaks of these waveforms, inverting the result and multiplying it by a factor of 60 in order to obtain an estimate of breathing rate in breaths per minute.

The results of these computations over the five-minute period are shown in FIGS. 5E and 5F respectively. The breathing rate is approximately 18 breaths/minute throughout the period, but the occurrence of peaks caused by cardiac as opposed to respiratory changes in the IP signal of FIGS. 5A and 5B gives rise to erroneously high breathing rates at t=1720, 1730, 1780, 1795, 1830 and 1860. Unfortunately no amount of optimisation of the FIR low-pass filter characteristics will ever completely remove the cardiac-synchronous information which is occasionally very prominent. For instance, in a hyperventilating patient, the breathing rate may be as high as 40 breaths per minute, which is similar to a slow heart rate. So separating signal from noise on a fixed basis is impossible.

Similarly, the two major instances D, E of movement artefact in the PPG signal of FIGS. 5C and 5D at t=1770 and t=1920 cause erroneously low estimates of breathing rates at D' and E' because there is a significant delay between the last valid peak and the first peak after the movement artefact. The estimate of breathing rate from the PPG signal is also more variable because occurrences of even slight movement artefact affect the tracking of the peaks of the PPG signal.

The present invention provides a method and apparatus for improving measurement of breathing rate by combining two measurements of it in a way which allows valid changes in the breathing rate to be distinguished from artefacts. In accordance with the invention two measurements of breathing rate made in different ways are combined with weights based on the amount of "confidence" in the measurement, to give an improved measurement or estimate of the actual breathing rate. The two measurements may, for example, be obtained using impedance pneumography and photoplethysmography, though other signals which include respiratory information (for instance ECG) can also be used instead of either of these signals, or in addition to them.

In more detail the invention provides a method of measuring breathing rate of a subject comprising the steps of: predicting the value of each of two independent measurements of the breathing rate, making two independent measurements of the breathing rate to produce two measured values, calculating the respective differences between the predicted values and the measured values, and combining the two measured values with weights determined by said differences.

The steps of prediction, measurement, calculation and combination may be repeated continuously. The predicted value for each of the independent measurements may be based on the preceding predicted value and the difference between the preceding predicted value and the preceding measurement.

The predicted value for each of the measurements may be calculated using a linear or non-linear predictive model, and the model may be adaptive, adapting in dependence upon the amount of process noise in the measurements.

In the combining of the two measured values, the weight of each value may vary inversely with the square of the difference between the predicted value and the measurement. In one example the two measured values may be combined according to the formula:

$$BR = BR_1 \frac{\sigma_2^2}{\sigma_1^2 + \sigma_2^2} + BR_2 \frac{\sigma_1^2}{\sigma_1^2 + \sigma_2^2}$$

where $BR_1$ and $BR_2$ are the two measured values of breathing rate and $\sigma_1$ and $\sigma_2$ are the differences between the two measured values and their respective predicted values.

The predicted values for the respective measurements may be based on respective models of the system, and the models may include estimates for process noise and sensor noise. The respective models may be mutually independent and may include the same estimates for process noise and sensor noise. The models may be Kalman filters.

Measurements for which the differences between both measured values and their predicted values exceed a predetermined threshold may be discarded. Further, artefacts, for instance caused by movement or heartbeat in the measurements may be identified based on the values of the differences between the measured values and their predicted values. This identification may be used to discard sections of the signal.

Thus with the present invention a prediction is made for each breathing rate measurement and the actual measurement is compared with its prediction. The difference is computed, which is termed the "innovation", and this innovation is used to calculate a weight which will be given to that measurement when it is combined with the other measurement, also weighted according to its innovation. The weights are calculated so that if the innovation on one measurement channel is high, whereas the innovation on the other measurement channel is low, the measurement from the low innovation channel is more heavily weighted. This is because a high level of innovation from one channel coinciding with a low innovation on the other channel is regarded as indicative of an artefact on the higher innovation channel.

BREIF DESCRIPTION OF THE DRAWINGS

It will be appreciated that the invention can be embodied using computer software, and thus the invention extends to a computer program for controlling and executing the method, or parts of it, and to a computer readable storage medium carrying the program. The invention also extends to corresponding apparatus for carrying out the method.

The invention will be further described by way of non-limitative example with reference to the accompanying drawings in which:—

FIG. 1 schematically illustrates apparatus in accordance with an embodiment of the invention connected to a patient;

FIGS. 2A and 2B show 30-seconds of IP and PPG signal respectively recorded from a patient;

FIGS. 3A and 3B show five-minutes worth of IP and PPG data respectively from the same patient as FIGS. 2A and B;

FIGS. 4A to D show the IP and PPG data of FIGS. 2A and B and processed versions of that data;

FIGS. 5A to F show IP and PPG data corresponding to FIG. 3, processed versions of that data and breathing rate estimates based on that data; and FIGS. 6A to G show the same data as FIGS. 5A to F and in addition in FIG. 6G a breathing rate estimate obtained by an embodiment of the present invention.

DETAILED DESCRIPTION OF EXAMPLE EMBODIMENTS

An embodiment of the invention will now be described in which the invention is applied in the medical field for the measurement of breathing rate using the two signals described above, namely the impedance pneumography and photoplethysmography signals. The results of applying this to the data of FIGS. 2 to 5 will be illustrated.

Figure 1:
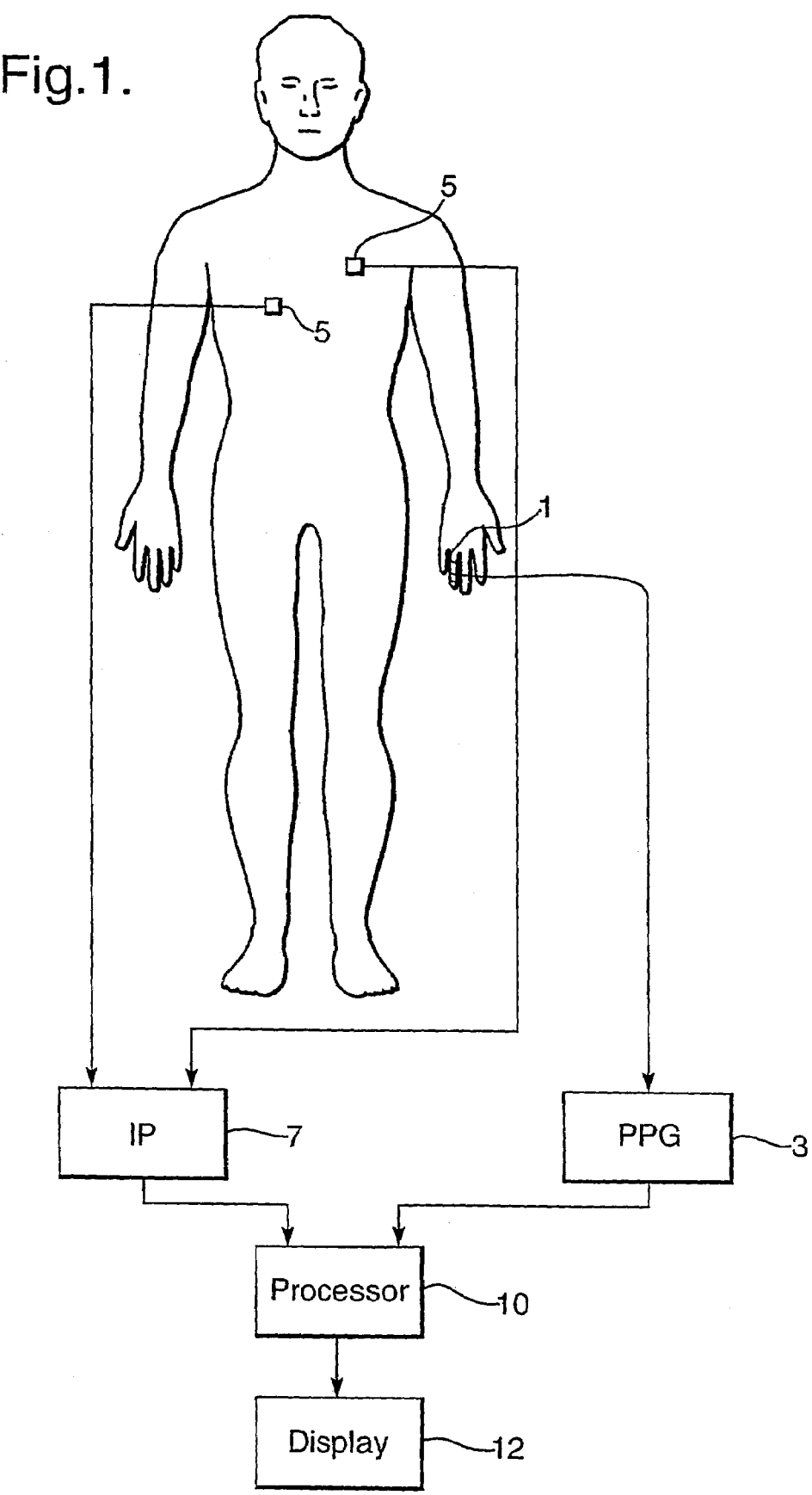
Figure 4A:
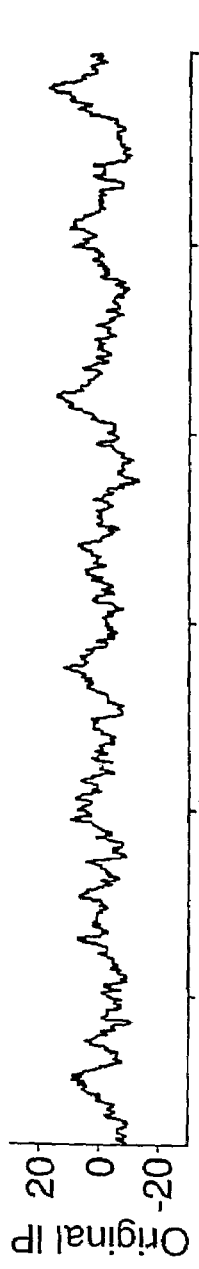
Figure 4B:
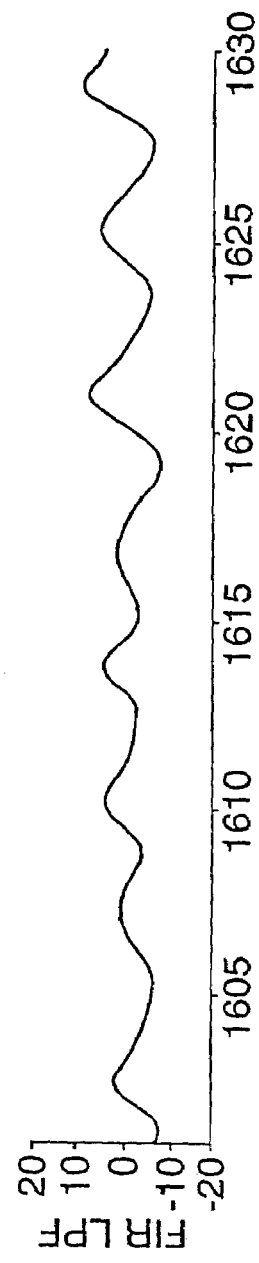
Figure 4C:
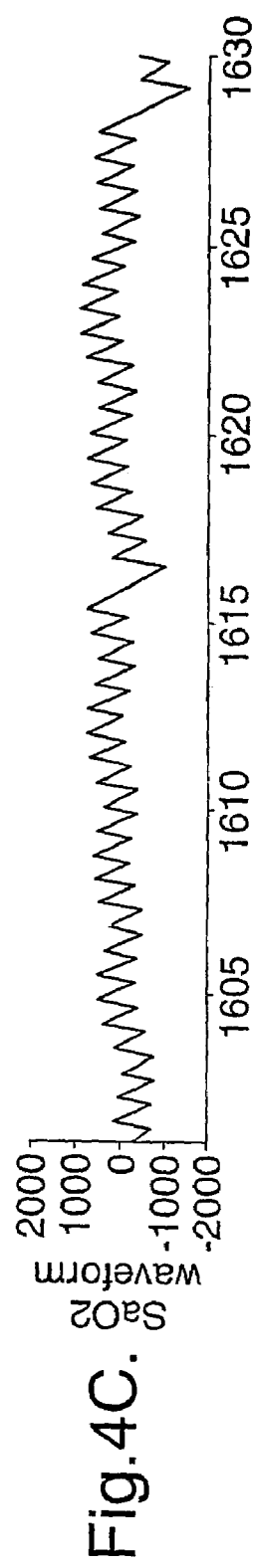
Figure 4D:
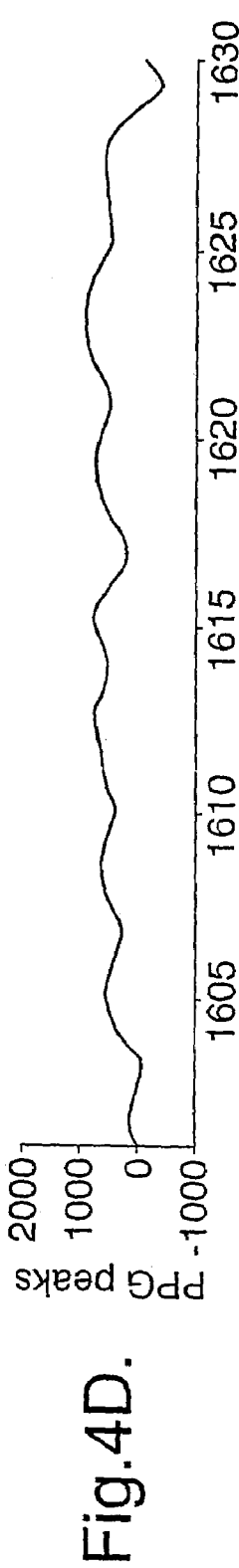
Figure 5A:
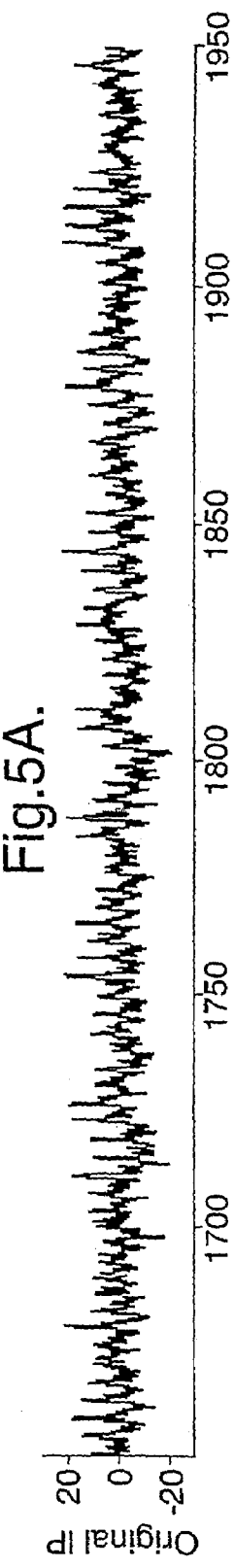
Figure 5B:
Figure 5C:
Figure 5D:
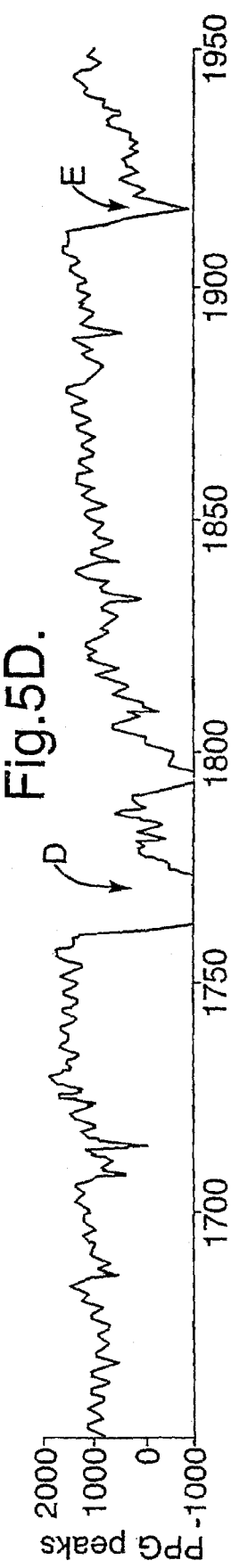
Figure 5E:
Figure 5F:
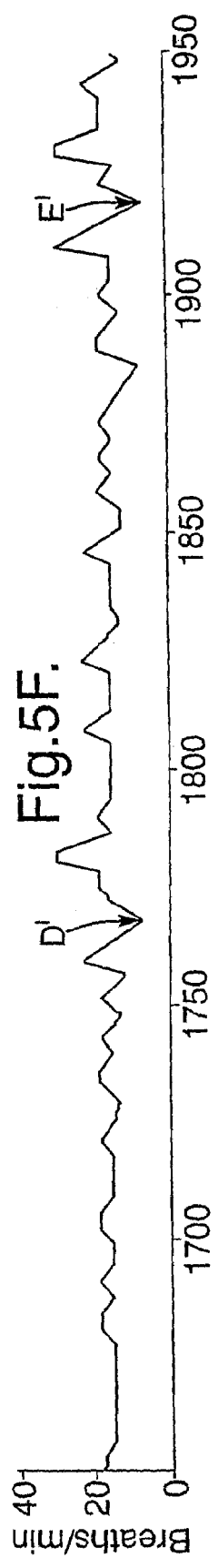

FIG. 1 schematically illustrates a breathing rate measurement apparatus in accordance with an embodiment of the invention. A PPG signal is obtained, as illustrated from a finger of a patient, though the signal can also be obtained from the earlobe, using a conventional PPG sensor 1 which is driven by and supplies its output to PPG apparatus 3. An IP signal is obtained by conventional IP equipment 7 using two electrodes 5 (though four electrodes may be used, with a pair for current injection and a pair for voltage measurement). The IP apparatus 7 and PPG apparatus 3 supply their signals to a processor 10 which processes the signals in the manner to be described below, and outputs a display of breathing rate on display 12. The display may be in graphical or numeric form, and may be combined with a display of others of the patient's vital signs. It will be appreciated that in this embodiment the IP apparatus 7 and PPG apparatus 3 produce an output to the processor 10 of raw signals of the types illustrated in FIGS. 6A and C. The processor 10 processes these signals to produce the signals of FIGS. 6B and D to G. However, the functions of the parts of the apparatus shown in FIG. 1 may be combined in different ways.

The processor 10 in essence runs a Kalman filter on each breathing rate signal, and then fuses the filtered signals to produce a fused estimate of the breathing rate.

The Kalman filter is a generic framework for analysing linear dynamical systems. Using the process model, the next state $x_{t+1}$ is computed from the current state $x_t$ using the transition matrix A, assuming first-order (Markov) dynamics. The observation model relates the observations $y_1$ to the state $x_1$ of the system via the observation matrix C. The process and observation noise are assumed to be independent and to have zero-mean, Gaussian probability distributions. In the normal physiological state, the breathing rate can be modelled with a scalar Kalman filter which assumes that the time to the next breath is the same as the interval since the previous breath plus some process noise characterising normal or breath-to-breath variability. Thus:

$$x_{t+1} = Ax_t + w \quad \text{(Process model)}$$

$$y_t = Cx_t + v \quad \text{(Observation model)}$$

In this embodiment it is assumed that C=1, i.e. the breathing rate is both the measurement and the state describing the process, with v as the sensor noise model. It is also assumed that the next breathing rate only varies by a small amount with respect to the current one, i.e. A=1 and w is the variance associated with breath-by-breath variability.

A scalar Kalman filter is run separately on each breathing rate signal, using the same process and measurement noise models for both channels. For each channel, the next state $x_{pred}$ is predicted using the Kalman filter equation (in which the next state is equal to the previous state plus the Kalman gain times the innovation). In this embodiment, the next measurement $y_{pred}$ is the same as the next state $x_{pred}$ (since C=1) and, after the next measurement of breathing rate, $y_{t+1}$, the innovation $\epsilon_{t+1}$ is computed, where:

$$y_{t+1} = y_{pred} + \epsilon_{t+1}$$

$\epsilon_{t+1}$ the difference between the actual value and the predicted value, should normally be a zero-mean white noise sequence. The square of the innovation, or variance, $\sigma_{t+1}^2 = \epsilon_{t+1}^2$, is the inverse of the "confidence" which is associated with the prediction. A robust estimate of the breathing rate is now obtained by mixing the two breathing rate estimates in inverse proportion to the variance associated with each one:

$$BR = \frac{\sigma_2^2}{\sigma_1^2 + \sigma_2^2} BR1 + \frac{\sigma_1^2}{\sigma_1^2 + \sigma_2^2} BR2$$

where $BR1 = y_{t+1}$ and $\sigma_1^2 = \sigma_{t+1}^2$ for channel 1 (filtered IP), with equivalent expressions for BR2 and channel 2 (PPG peaks). The innovation variance and the Kalman gain are also calculated to update the state estimate in readiness for the next cycle. An example of an implementation of this model in MATLAB is given in Appendix 1. That example is general and will work for vector quantities though in this embodiment the quantities are scalar. It can be seen from Appendix 1 that the predicted breathing rate for each new measurement cycle (xnew) is equal to the previously predicted value (xpred) plus the Kalman gain K times the innovation e. The Kalman gain K is derived from the predicted variance Vpred and the measurement variance R. The predicted variance is derived from the previous predicted variance and the process noise Q. To start the process off it is initialised using an initial value of the breathing rate as 15 and an initial value of the state variance of 40. The process noise in the Q in this embodiment is set to 10 and the measurement noise variance R is set to 100.

It will be clear from the implementation that, as normal with a Kalman filter, the variance and Kalman gain are not dependent on the measurement values. The measurement values are only used in the new prediction of breathing rate via the innovation e. Thus it will be noted that for the constant values of Q and R used in this example the Kalman gain K tends to about 0.2 and the state co-variance V tends to about 27. However, K can be made adaptive by modifying the values for the variance constants. Q and R, preferably the process variance Q, according to the type of process being encountered.

The advantages of this method can be appreciated from four possible contexts:

1. normal breathing: low innovations on both channels; both measurements BR1 and BR2 are weighted equally.
2. valid change seen on both channels: the subject begins to breathe more quickly or more slowly due to a physiological change; although the innovation is high, it is high for both channels, and so both (valid) measurements are again weighted equally.
3. artefact on one channel: high innovation on one channel only; the information from that channel is ignored because it is given a low weighting (high variance).
4. artefact on both channels: the information is corrupted on both channels. Prolonged movement artefact, however, is characterised by high values of innovation on both channels for a sustained period of time and this can be the basis for discarding sections of data corrupted by movement artefact.

Note that a fused estimate is computed every time a new measurement of BR1 or BR2 becomes available, i.e. twice during the respiration cycle (once for each sensor).

It should also be noted that in the event of a problem with an electrode such as it becoming detached or falling off, or of signal loss through some other cause, this would result in a high innovation and thus a low weighting for that channel.

FIG. 6G illustrates the result of combining the breathing rate signals of FIGS. 6E and F in this way.

FIG. 6G illustrates the result of applying the invention to the breathing rate signals of FIGS. 6E and F obtained respectively from the impedence pneumography and PPG signals of FIGS. 6A to D. Thus the original IP signal of FIG. 6A is filtered using a finite impulse response low-pass filter to produce the processed signal of FIG. 6B. The PPG signal of FIG. 6C is subjected to peak tracking as described above to produce a respiratory waveform of FIG. 6D. Each of these is used to estimate a breathing rate, by calculating the interval between two successive peaks, inverting the result and multiplying it by a factor of 60. These two breathing rate estimates are shown in FIGS. 6E and F. The two breathing rate estimates BR1 and BR2 are subjected to the Kalman filtering and fusing the process described above and this gives the fused breathing rate estimate of FIG. 6G. It can be seen that apparent changes in breathing rate which appear only on one channel (for instance marked F on FIG. 6E or the changes D' and E' on FIG. 6F) are removed from the fused breathing rate estimate. However, a change in breathing rate on both channels, such as marked G in FIGS. 6E and 6F, appears as G' on the fused estimate of FIG. 6G.

APPENDIX 1

```
load -ascii ip_resprate;
data_file = ip_resprate;
time = data_file(:,1);
br = data_file(:,2);
start = 1
stop = size(data_file),1);
fprintf('number of breaths detected = %d \n', stop);
br_limit = 40;
            % X(t+1) = A X(t)+noise(Q) - process model with Q as variance of noise
w
            % Y(t) = C X(t)+noise(R) - measurement model with R as variance of
noise v
```

APPENDIX 1-continued

```
ss = 1;                  % state size - sets to one dimensional, ie scalar though routine works for
                           vectors
os = 1;                  % observation size      - sets to one dimensional, ie scalar
A = [1];                 % assume x(t+1)=x(t)
C = [1];                 % assume y=x
Q = 10.0*eye(ss);        % process noise          - eye is the identity matrix in MATLAB -here just
                                                   unity
R = 100.0*eye(os);       % measurement noise variance
initx = [15];            % initial state value(BR of 15 bpm)
initV = 40*eye(ss);      % initial state variance
xnew = initx;            % - initialisation
Vnew = initV;
no_update = 0;
n = 1;
for i = start:stop % - start of cycle
    x = xnew;                    % update from previous cycle
    V = Vnew;                    % update from previous cycle
    xpred = A*x;                 % prediction of state
    Vpred = A*V*A' + Q;          % prediction of state covariance, A' is transpose of A
    ypred(i) = C*xpred;          % prediction of measurement
    y(i) = br(i);                % "make measurement"
    t(i) = time(i);
% if y(i) == br_limit no_update = 1; %artefact
% else no_update = 0;
% end
    e = y(i) – ypred(i);         % calculate innovation
    innov(i) = e;                % for plotting
    sigma2(i) = e*e;             % variance for saving
    S = C*Vpred*C' + R;          % innovation covariance
    Sinv = inv(S);               % invert S to compute Kalman gain
    K = Vpred*C' *Sinv;          % Kalman gain matrix
    if no_update == 0            % only update if no artefact
        xnew = xpred + K*e;          % update state by the innovation
                                       controlled by the Kalman gain
        Vnew = (eye(ss) – K*C)*Vpred;  % update state covariance
    end
    if i – (n*10) == 0
        fprintf( '\n %d0 breaths processed ', n);
        n = n + 1;
    end
end
```

The invention claimed is:

1. A method of measuring breathing rate of a subject comprising the steps of: predicting a value of each of two independent measurements of the breathing rate for two independent measurement channels, making two independent measurements of the breathing rate via said two independent measurement channels to produce two measured values of the breathing rate, calculating respective differences between the predicted values and the measured values for each of said two independent measurement channels, and combining the two measured values with weights determined by said differences.

2. A method according to claim 1 in which the steps of prediction, measurement, calculation and combination are repeated continuously, the predicted value for each of the two independent measurements being based on the preceding predicted value and the difference between the preceding predicted value and the preceding measurement.

3. A method according to claim 2 in which the predicted value for each of the two independent measurements is calculated by using a linear predictive model.

4. A method according to claim 2 in which the predicted value for each of the two independent measurements is calculated by using a non-linear predictive model.

5. A method according to claim 2 in which the predicted value for each of the two independent measurements is calculated by using an adaptive predictive model, and wherein the model adapts in dependence upon the amount of process noise in the measurements.

6. A method according to claim 1 in which in the step of combining the two measured values the weight of each value varies inversely with the square of the difference between the predicted value and the measurement.

7. A method according to claim 6 in which the two measured values are combined according to the formula:

$$BR = BR_1 \frac{\sigma_2^2}{\sigma_1^2 + \sigma_2^2} + BR_2 \frac{\sigma_1^2}{\sigma_1^2 + \sigma_2^2}$$

where $BR_1$ and $BR_2$ are the two measured values, and $\sigma_1$ and $\sigma_2$ are the differences between the two measured values and their respective predicted values.

8. A method according to claim 1 in which the predicted values for the respective measurements are based on respective models of the system.

9. A method according to claim 8 in which the models of the system include estimates for process noise and sensor noise.

10. A method according to claim 8 in which the respective models of the system are mutually independent.

11. A method according to claim 10 in which the respective models of the system include the same estimates for process noise and sensor noise.

12. A method according to claim 8, in which the respective models of the system are Kalman filters.

13. A method according to claim 1 further comprising the step of discarding series of measurements for which the differences between both measured values and their predicted values exceed a predetermined threshold for a predetermined period of time.

14. A method according to claim 1 in which the two independent measurements are made by impedance pneumography and photoplethysmography.

15. A method according to claim 1 in which there are more than two measurements.

16. A method according to claim 1 further comprising the step of identifying artefacts in the measurements based on the values of the differences between both measured values and their predicted values.

17. A computer program encoded on a computer-readable medium and comprising program code which, when executed, performs the method of claim 1.

18. Apparatus for measuring breathing rate of a subject, the apparatus comprising:
    two independent measurement channels for receiving two independent measurements of a breathing rate as two measured values of the breathing rate; and
    a processor configured to predict values of each of the two independent measurements of the breathing rate for the two independent measurement channels, to calculate respective differences between the predicted values and the measured values for each of said two independent measurement channels, and to combine the two measured values with weights determined by said differences.

19. The apparatus according to claim 18, further comprising:
    a display for displaying the breathing rate.

20. Apparatus for measuring breathing rate of a subject, the apparatus comprising:
    first and second independent measurement channels for providing respective independent measurements of a breathing rate as first and second measured values of the breathing rate; and
    a processor configured to predict values of each of the first and second independent measurements of the breathing rate for the respective first and second independent measurement channels using respective Kalman filters, to calculate respective differences between the predicted values and the measured values for each of the first and second independent measurement channels, and to combine the first and second measured values with weights determined by the differences.

* * * * *

UNITED STATES PATENT AND TRADEMARK OFFICE
CERTIFICATE OF CORRECTION

PATENT NO.       : 7,318,808 B2
APPLICATION NO.  : 10/498673
DATED            : January 15, 2008
INVENTOR(S)      : L. Tarassenko et al.

It is certified that error appears in the above-identified patent and that said Letters Patent is hereby corrected as shown below:

On the cover page, in item (86), delete "PCT/GB20/05684" and insert --PCT/GB02/05684-- therefor.

Signed and Sealed this

Twentieth Day of May, 2008

JON W. DUDAS
*Director of the United States Patent and Trademark Office*